United States Patent [19]
Phadke et al.

[11] Patent Number: 5,750,401
[45] Date of Patent: May 12, 1998

[54] CULTURAL MEDIUM FOR BAMBOO SHOOT SPROUTING AND MULTIPLICATION AND A METHOD FOR SPROUTING AND MULTIPLICATION OF BAMBOO PLANTLETS

[75] Inventors: Chandrashekhar Hari Phadke; Nazifa Najmuddin Nagarqala; Varsha Anil Parasharami; Rajani Satish Nadgauda; Anthony Francis Mascarenhas, all of Pune, India

[73] Assignee: C.S.I.R., New Delhi, India

[21] Appl. No.: 511,074

[22] Filed: Aug. 3, 1995

[51] Int. Cl.$^6$ .................................................. C12N 5/00
[52] U.S. Cl. .................... 435/430; 435/410; 435/420; 435/431
[58] Field of Search ........................ 435/240.45, 240.4, 435/240.54, 240.48, 325, 410, 420, 430, 431

[56] References Cited

U.S. PATENT DOCUMENTS 5,334,530  8/1994  Woods et al. ..................... 435/240.48

OTHER PUBLICATIONS

A Revised Medium For Rapid Growth And Bio . . . Cultures: Murashige etal: Physiol. Plant., 15, 1962: pp. 473–497.

*Primary Examiner*—Leon B. Lankford, Jr.
*Attorney, Agent, or Firm*—Ladas & Parry

[57] ABSTRACT

The present invention relates to a growth medium for the sprouting, multiplication and rooting of bamboo nodal buds from mature bamboo species, via plant tissue culture method, which method comprises a multistage culturing process by collecting a suitable explant from the best bamboo clumps which is first cultured on a solid medium, that induces sprouting of the dormant buds. The sprouts are then further multiplied in an aqueous medium without any solidification. After a certain period, when shoots have been multiplied sufficiently under a proper photoperiod of light and dark, the shoots are transferred to the medium containing low concentration of salts and hormones. Culturing to this point is carried out under subdued light or darkness. Subsequent shifting to hormone free medium after a particular time, the time ranges between 24 hours to 96 hours, develops root initiation. The plantlets thus formed may then be transferred to soil for further growth.

11 Claims, No Drawings

CULTURAL MEDIUM FOR BAMBOO SHOOT SPROUTING AND MULTIPLICATION AND A METHOD FOR SPROUTING AND MULTIPLICATION OF BAMBOO PLANTLETS

The present invention relates to a novel medium for the sprouting, multiplication and rooting of bamboo nodal buds from mature bamboo species and a multistage bamboo-tissue culturing method.

BACKGROUND OF THE INVENTION

Bamboo is one of the most useful plants known to man and is arguably the fastest growing plant species on the earth. Bamboo which is popularly referred to as "poor man's timber" comprises approximately 75 genera and 1250 species. It is a traditional crop in Asian countries where it is employed for food, fibre, fuel, handicrafts and, essentially, in the paper pulp industry. The demand for bamboo throughout the world is an ever-increasing one and such demand regularly fails to be met entirely.

It has been clear to researchers for some time that the only way in which the demand for bamboo can be met is by propagation of additional plants by conventional methods. Unfortunately, in the case of bamboo, supply cannot be met with the standard procedures of propagation from seeds, by air layering or from rhizomes and culm cuttings. The scientists therefore thought that the only method for getting large number of plants of bamboo is through clonal multiplications. The process involves multiplication of tissues on an artificial medium. For instance, one of the prior art propagation media is the one formulated by Murashige and Skoog(MS) in 1962. This medium comprised a mixture of inorganic salts in combination with organic constituents such as sucrose, aminoacids and plant growth regulators. Stated more specifically, this medium, referred to as "Composition I" for convenience, was made up of the following ingredients.

|  | Concentration mg/L |
|---|---|
| (a) Mineral salts | |
| $NH_4NO_3$ | 1650 |
| $KNO_3$ | 1900 |
| $CaCl_2, 2H_2O$ | 440 |
| $MgSO_4.7H_2O$ | 370 |
| $KH_2PO_4$ | 170 |
| KI | 0.83 |
| $H_3BO_3$ | 6.20 |
| $MnSO_4.4H_2O$ | 22.303 |
| $ZnSO_4.7H_2O$ | 8.60 |
| $Na_2MoO_4.2H_2O$ | 0.25 |
| $CuSO_4.5H_2O$ | 0.025 |
| $CoCl_2.6H_2O$ | 0.025 |
| $Na_2EDTA$ | 37.30 |
| (Sodium salt of ethylene diamine tetra acetic acid) | |
| $FeSO_4.7H_2O$ | 27.80 |
| (added as chelate with $Na_2EDTA$) | |
| (b) Organic components | |
| Sucrose | 20,000 |
| myo-Inositol | 100 |
| Thiamine hydrochloride | 0.1 |
| Nicotinic acid | 0.5 |
| Pyridoxine hydrochloride | 0.5 |
| Glycine | 2.0 |
| Edamin | 1,000 |

Composition I was employed for the tissue culture of tomato, teak, eucalyptus, rose-wood, ferns, gerberas and so on with varying degrees of success. Unfortunately, it was not found suitable for propagation of mature explants of the bamboo species, probably because bamboo is a monocotyledonous woody perennial and was therefore modified further to meet our requirements viz. clonal propagation of bamboo species using nodal bud explant. In the circumstances, the provision of a method and a tissue culture medium for the clonal multiplication of bamboo plantlets from mature elite superior clumps of bamboo in which the elite traits are retained in the plantlets would be a major breakthrough in bamboo propagation.

With this in view, research was carried out by the applicants. The project involved the clonal multiplication of three different species namely Eucalyptus, Salvadora and Bamboo. The research in question succeeded in developing culture procedures for mature trees of Eucalyptus and *Salvadora persica*. Regrettably a similar process for the propagation of mature trees from bamboo could not be developed. In fact, in respect of bamboo, only seedling explants could be multiplied. Fortunately, the research workers did not abandon their research but continue to work on mature bamboo trees. As a result of these efforts, a process has now been developed exploring a specific plant tissue culture method whereby complete plantlets can be regenerated from mature *Bambusa arundinacea, Dendrocalamus strictus* and is considered more than possible that such process and medium will be successful in respect of other bamboo species such as *Dendrocalamus brandisii* and *Bambusa vulgaris, Bambusa oxydenthera, Bambusa balcoa* etc. In point of fact, the present invention envisages a novel culture medium for the bud sprouting and clonal multiplication of bamboo shoots from mature bamboo plants as well as for the initiation of roots on sprouted multiple shoots forming complete plantlets.

OBJECT OF THE INVENTION

The first object of the present invention relates to a growth medium for the sprouting, multiplication and rooting of bamboo nodal buds from mature bamboo species.

The second object of the present invention relates to a bamboo-tissue culturing method to produce bamboo plants specially plantlets.

The other object of the present invention provides a multistage tissue culturing method which comprises of collecting a suitable explant from the best bamboo clumps selected on the basis of the number of culms per clump, internodal distance, quality of culms, disease resistance, fibre length and absence of excessive branching, is first cultured on a solid medium, that induces sprouting of the dormant buds. The sprouts are then further multiplied in an aqueous medium without any solidification. After a period of several days, when shoots have been multiplied sufficiently under a proper photoperiod of light and dark, the shoots are transferred to the medium containing low concentration of salts and hormones. Culturing to this point is carried out under subdued light or darkness. Subsequent shifting to hormone free medium after a particular time, the time ranges between 24 hours to 96 hours develops root initiation. The plantlets thus formed may then be transferred to soil for further growth. The method has been successful with a wide range of species and with numerous genotypes that could not previously be propagated by mature tree tissue culture techniques.

DETAILED DESCRIPTION OF THE PREFERRED EMBODIMENTS

The process of the present invention is not limited to any single culture medium or to the use of specific growth hormones. Any of number of well known media, such as Murashige and Skoog (1962) may be used. The particular auxins and cytokinins used will depend somewhat on the species being cultured and even on the particular genotype within that species. This is something that can not be readily predicted but can easily be delimited experimentally. However, according to a principal embodiment, the present invention provided a culture medium for the growth and clonal multiplication of bamboo plant shoots which comprises compounds capable of providing as elements aluminum, boron, chlorine (chloride), chromium, cobalt, copper, iodine, iron, lead, magnesium, manganese, molybdenum, nitrogen (nitrates), potassium, phosphorous (phosphates), silicon, sodium, sulphur (sulphates), titanium, vanadium and zinc, organic components selected from sucrose, glucose, fructose, myoinositol, thiamine hydrochloride, nicotinic acid, pyridoxine hydrochloride, glycine, kinetin (Kn), benzyl aminopurine (BA), malt extract, yeast extract, coconut milk and agar agar in an aqueous medium.

The preferred aspect of the invention relates to a culture medium said elements (mineral salts) and organic components are present in the following ranges.

| Mineral salts | | concentration (mg/L) |
|---|---|---|
| K | (salts of potassium) | 96.69 to 1237 |
| $NH_4$ | (salts of ammonium) | 33.75 to 405 |
| Mg | (salts of magnesium) | 5.55 to 47 |
| Ca | (salts of calcium) | 11.92 to 0.136 |
| B | (salts of boron) | 0.13 to 1.4 |
| Al | (salts of aluminum) | 0.1 to 0.0008 |
| Mn | (salts of manganese) | 0.74 to 6.65 |
| $PO_4$ | (phosphate salts) | 52.94 to 174 |
| $NO_3$ | (nitrate salts) | 269.44 to 3754 |
| $SO_4$ | (Sulphate salts) | 59.75 to 914 |
| Cl | (chloride salts) | 21.00 to 241 |
| Fe | (as a chelate with ethylene diamine tetra acetic acid) | 0.50 to 5.25 |
| Co | (salts of cobalt) | 0.0006 to 0.01 |
| Cu | (salts of copper) | 0.0006 to 0.008 |
| Cr | (salts of chromium) | 0.01 to 0.02 |
| Ti | (salts of titanium) | 0.00 to 0.013 |
| V | (salts of vanadium) | 0.00 to 5.45 |
| Zn | (salts of zinc) | 0.23 to 2.73 |
| Mo | (salts of molybdenum) | 0.017 to 0.11 |
| Si | (salts of silicon) | 0.00 to 0.4 |
| Na | (salts of sodium) | 0.081 to 0.65 |
| Pb | (salts of lead) | 0.00 to 0.12 |
| I | (salts of iodine) | 0.017 to 1.15 |
| Cl | (salts of chlorine) | 21 to 241 |
| Organic compounds | | |
| Sucrose | | 20,000 to 50,000 |
| Glucose | | 20,000 to 50,000 |
| Fructose | | 20,000 to 50,000 |
| Myo-Inositol | | 10.75 to 130 |
| Thiamine hydrochloride | | 0.02 to 0.15 |
| Pyridoxine hydrochloride | | 0.075 to 1.75 |
| Nicotinic acid | | 0.05 to 1.5 |
| Glycine | | 0.3 to 3.5 |
| Kinetin | | 0.00 to 0.80 |
| Benzyl adenine | | 0.00 to 0.80 |
| Indolebutyric acid | | 0.0 to 3.5 |
| Indoleacetic acid | | 0.0 to 3.5 |
| Indolepropionic acid | | 0.0 to 3.5 |
| Naphthaleneacetic acid | | 0.0 to 3.5 |
| Malt extract | | 0.00 to 200.00 |
| Yeast extract | | 0.00 to 500.00 |
| Coconut milk (added as mL/L) | | 0.00 to 200.00 |
| Agar (for solidification) | | 4,000 to 4,500 |

According to yet another preferred feature, the elements and organic components are present in the culture medium for growth and clonal multiplication of bamboo plantlets in the following ranges

| Composition II | |
|---|---|
| | Concentration mg/L |
| (a) Mineral salts | |
| $KNO_3$ | 1000 to 3198 |
| $NH_4NO_3$ | 772 to 2315 |
| $MgSO_4.7H_2O$ | 223 to 476.5 |
| $CaCl_2.2H_2O$ | 176 to 498.8 |
| $MgSO_4.7H_2O$ | 223 to 476.5 |
| $KH_2PO_4$ | 124.6 to 249.2 |
| $H_3BO_3$ | 2.9739– 8.0068 |
| $Al.NH_4 (SO_4)_2.12H_2O$ | 0.1176– 0.01344 |
| $MnSO_4.4H_2O$ | 11.7763– 27.004 |
| COOK.COOTi (Salt of titanium) | 0.02382– 0.04423 |
| $NH_4VO_3$ | 0.023– 12.51 |
| $FeSo_4.7H_2O$ (added as chelate with $Na_2EDTA$) | 11.45– 26.13 |
| $CoCl_2.6H_2O$ | 0.1009– 0.04036 |
| $CrO_3$ | 0.01923– 0.03846 |
| $CuSO_4. 5H_2O$ | 0.1123– 0.02995 |
| $Na_2O_3Si.9H_2O$ | 0.5059– 4.0475 |
| $ZnSO_4.7H_2O$ | 4.0022– 12.0066 |
| $Na_2MoO_4.2H_2O$ | 0.1764– 0.2773 |
| KI | 0.8066– 4.882 |
| $C_6H_6O_4.Pb.3H_2O$ | 0.1464– 0.2197 |
| $Na_2EDTA,2H_2O$ | 0.6557– 5.2622 |
| (b) Organic components | |
| Sucrose | 20,000.00 50,000.00 |
| Glucose | 20,000.00 50,000.00 |
| Fructose | 20,000.00 50,000.00 |
| myo-Inositol | 75.00 130.00 |
| Thiamine hydrochloride | 0.08 0.15 |
| Nicotinic acid | 0.20 1.50 |
| Pyridoxine hydrochloride | 0.30 1.75 |
| Glycine | 1.20 3.50 |
| Kinetin | 0.20 0.80 |
| Benzyl aminopurine | 0.20 0.80 |
| Malt extract | 50.00 200.00 |
| Yeast extract | 100.00 500.00 |
| Coconut milk (added as ml/L) | 20.00 120.00 |
| Agar agar (for solidification) | 4,000.00 4,500.00 |

It has been found that the combination of ingredients in the culture medium cause higher photosynthetic activity and a modification in cellular structure of the parent plants thereby permitting higher intake of nutrients as a result of the increased permeability of the cell membrane, different enzymic activities and increased protein synthesis, as shoot growth was weak and pale yellow.

According to a further embodiment, the invention provides an improved culture medium for the root initiation of clonally multiplied, bamboo sprouts, which comprises salts capable of providing as elements aluminum, boron, chlorine (chloride), chromium, cobalt, copper, iodine, iron, lead, magnesium, manganese, molybdenum, nitrogen (nitrates), potassium, phosphorous (phosphates), silicon, sodium, sulphur (sulphates), titanium, vanadium and zinc, and organic components selected from sucrose, glucose, fructose, myo-inositol, thiamine, hydrochloride, nicotinic acid, pyridoxine hydrochloride, glycine, indolebutyric acid (IBA), indoleacetic acid (IAA), indolepropionic acid (IPA) and naphthalene acetic acid (NAA).

According to a still further feature, the elements, and organic components are present in the culture medium for root initiation in the following ranges

| Composition - III | |
|---|---|
| | Concentration mg/L |
| (a) Mineral salts | |
| $KNO_3$ | 250 to 1600 |
| $NH_4NO_3$ | 150 to 898.8 |
| $MgSO_4.7H_2O$ | 56.27 to 238.26 |
| $CaCl_2.2H_2O$ | 43.72 to 249.4 |
| $KH_2PO_4$ | 75.82 to 303.39 |
| $H_3BO_3$ | 0.7434 to 4.0 |
| $MnSO_4.4H_2O$ | 3 to 13.52 |
| $FeSO_4.7H_2O$ | 2.887 to 13.09 |
| (added as chelate with $Na_2EDTA$) | |
| $CoCl_2.6H_2O$ | 0.0024 to 0.02 |
| $CuSO_4.5H_2O$ | 0.0023 to 0.016 |
| $ZnSO_4.7H_2O$ | 1 to 6.02 |
| $Na_2MoO_4.2H_2O$ | 0.043 to 0.151 |
| KI | 0.072 to 2.46 |
| (b) Organic components | |
| Sucrose | 20,000 to 50,000 |
| Glucose | 20,000 to 50,000 |
| Fructose | 20,000 to 50,000 |
| myo-Inositol | 18.75 to 65.00 |
| Thiamine hydrochloride | 0.02 to 0.075 |
| Nicotinic acid | 0.05 to 0.75 |
| Pyridoxine hydrochloride | 0.075 to 0.875 |
| Glycine | 0.3 to 1.75 |
| Indolebutyric acid | 1.00 to 3.5 |
| Indoleacetic acid | 1.00 to 3.5 |
| Indolepropionic acid | 1.00 to 3.5 |
| Naphthaleneacetic acid | 1.00 to 3.5 |

The invention also includes within its scope a method for the growth and multiplication from mature elite bamboo species of bamboo plantlets which retain the elite traits of the parent plants.

A critical key to the present invention is the balance of different ingredients of the media used in the various culturing stages. Although the ingredients noted in composition II and III proved more suitable for two bamboo species described (*Bambusa arundinacea* and *Dendrocalamus strictus*), it may prove suitable for other bamboos also with different permutation and combinations.

All compounds (salts) capable of providing different elements indicated in the description will work in the invention provided the final concentration of each salt in the medium is within the range given and no extra elements are added in the medium.

The two compositions i.e. two culture media described are essential for the completion of the whole method of bamboo plant production. Elimination of either composition will not be a full method.

The invention will now be described in greater detail in the following non limitative examples:

EXAMPLE-1

The following schedule of treatments has been very successfully used for the growth of plantlets by clonal multiplication of tissues from mature bamboos (*Bambusa arundinacea, Dendrocalamus brandisii* and *Dendrocalamus strictus*. Explants were nodal cuttings from mature bamboo plants. Explants were collected from different forest areas specially located in the southern part of India and brought to the laboratory after sealing the ends with wax. Immediately, these were processed for surface sterilization using a method described below.

Nodal buds from mature clumps of the bamboos were collected, cleaned washed and were surface sterilized with ethanol, a detergent antiseptic solution and finally with $HgCl_2$ (0.05% to 0.15% W/V).

Stage I: Sprouting (Induction)

Surface sterilized buds were kept on a solid culture medium (it is the medium which is not in liquid form but is in solid form) described below (Composition IV) in an environment at 25° C.±2° C. with 16 hrs light under 500 to 1500 lux intensity (photoperiod) and 8 hrs dark alternately. The duration of the time dependent on a particular genotype being cultured. At the end of this time, the dormant buds sprouted giving out new shoots which we have termed as 'sprouting of buds'. These sprouted buds are characterized with tender juvenile shoots measuring approximately 2 to 6 cm. This varies with genotype and the season when the buds are collected.

| Composition IV | |
|---|---|
| | Concentration mg/L |
| (a) Mineral salts | |
| $KNO_3$ | 1200 |
| $NH_4NO_3$ | 998.75 |
| $MgSO_4.7H_2O$ | 399.98 |
| $CaCl_2.2H_2O$ | 299.97 |
| $KH_2PO_4$ | 509.71 |
| $H_3BO_3$ | 4.998 |
| $AlNH_4(SO_4)_2.12H_2O$ | 0.1 |
| $MnSO_4.4H_2O$ | 19.895 |
| COOK.COOTi | 0.027 |
| $NH_4VO_3$ | 0.034 |
| $FeSo_4.7H_2O$ | 15.082 |
| (added as chelate with $Na_2EDTA$) | |
| $Na_2O_3Si.9H_2O$ | 0.6071 |
| $CoCl_2.6H_2O$ | 0.02422 |
| $CrO_3$ | 0.03269 |
| $CuSO_4.5H_2O$ | 0.01964 |
| $ZnSO_4.7H_2O$ | 5.9813 |
| $Na_2MoO_4.2H_2O$ | 0.2622 |
| KI | 1.2034 |
| $C_6H_6O_4.Pb.3H_2O$ | 0.1647 |
| $Na_2EDTA$ | 1.0524 |
| (b) Organic components: | |
| Sucrose | 25,000.00 |
| Glucose | 0.00 |
| myo-Inositol | 100.00 |
| Thiamine hydrochloride | 0.10 |
| Nicotinic acid | 0.40 |
| Pyridoxine hydrochloride | 0.30 |
| Glycine | 1.50 |
| Kinetin | 0.2 |
| Benzyl aminopurine | 0.3 |
| Malt extract | 50.00 |
| Coconut milk (added mL/L) | 50.00 |
| Agar agar (for solidification) | 4,000.00 |

Stages II: Maintainance and Multiplication of Shoot Cultures

At early stages these tender shoots from the sprouting buds obtained in the induction stage were placed on a medium with the composition same as composition IV except that it contains no agar, as a result is liquid in state (Composition V). The temperature and photoperiod were 25° C.±2° C. and 16 and 8 hrs light and dark alternately. The incubation condition was different since the culture vessels were put on a rotary shaker with 80 to 120 rpm. The shoots developed further giving rise to multiple shoots. The time period to obtain this varies from 20–35 days depending on the genotype.

EXAMPLE-2

Cultures were made as above on the same medium used respectively at different stages except that sucrose from the induction and multiplication medium was replaced by the same concentration of glucose the only change made in composion IV is that sucrose was replaced by glucose i.e. (Composition VI). Rest of the temperatures and other environmental conditions were kept as described in Example-1 for both the stages. At a stage I bud sprouting was obtained which was however delayed as compared to that described in Example-1 with the same genotype. These sprouted buds on transfer to multiplication medium without agar grew further giving rise to multiple shoots. The shoots multiplied with a slow rate as compared to that in presence of sucrose. It appears that most if not all, sugars can give rise to bud induction and multiplication though the response may be variable with individual sugars.

EXAMPLE-3

Stage III Rooting of In vitro bamboo shoots

Shoots obtained in multiplication stage on Composition V were removed and placed on Composition VII described below. Hormone regime was altered completely and the cytokinins were replaced by auxins. The temperature is between 25° C., (±2 ° C.) with subdued light or darkness for a period of 48–120 hrs. The length of time dependent on a particular genotype being cultured. Thereafter the shoots were removed from the media and transferred to respective media from which auxins had been excluded. In fresh media the shoots were incubated under 500 to 1500 lux light intensity for 16 hrs. with 8 hrs. dark period each day. After 10 to 25 days it was found that shoots had grown roots thus developing in complete plantlet depending on the species and the genotype.

| Composition VII | |
|---|---|
| | Concentration mg/L |
| (a) Mineral salts | |
| $KNO_3$ | 333.35 |
| $NH_4NO_3$ | 199.73 |
| $MgSO_4.7H_2O$ | 74.92 |
| $CaCl_2.2H_2O$ | 58.31 |
| $KH_2PO_4$ | 41.528 |
| $H_3BO_3$ | 1.00 |
| $MnSO_4.4H_2O$ | 3.979 |
| $FeSo_4.7H_2O$ (added as chelate with $Na_2EDTA$) | 3.832 |
| $CoCl_2.6H_2O$ | 0.0032 |
| $CuSO_4.5H_2O$ | 0.0314 |
| $ZnSO_4.7H_2O$ | 1.319 |
| $Na_2MoO_4.2H_2O$ | 0.0580 |
| KI | 0.0837 |
| (b) Organic components | |
| Sucrose | 10,000 |
| myo-Inositol | 25.00 |
| Thiamine hydrochloride | 0.027 |
| Nicotinic acid | 0.067 |
| Pyridoxine hydrochloride | 0.1 |
| Glycine | 0.4 |
| Indolebutyric acid | 1.0 |

EXAMPLE-4

The shoots obtained in multiplication stage described under Example-1 were removed and placed on medium (Composition VIII). This medium was same as described in Example-3. The only difference in Composition VII and VIII is that Indole butyric acid (IBA) of VII was replaced by the same concentration of Naphthalene acetic acid (NAA) i.e. (Composition VIII). Rest of the physical conditions were kept constant. After shifting the shoots to hormone free medium, rooting was observed. This was however, associated with callus formation at the base of the shoots and the roots obtained were loosely attached to the shoots compared to that in Example-3.

Different auxins may prove suitable for a root growth. However, it was noticed that IBA treatment gave 80 to 90% root formation as against NAA treatment, where rooting was only 8 to 12%. The auxins can be used in combinations depending on the type of genotype and species to be grown.

Stage 4: plant Growth

Plantlets from stage 3 of Example-3 and Example-4 were removed from the culture medium and planted in a soil comprising equal parts of river site soil and sand.

To the present time 6 different genotypes belonging to both the species (Bambusa arundinacea and Dendrocalamus strictus) have been cultured through stages 1,2,3 and the plantlets have been successfully transferred to soil and are growing with good vigor. It was clearly noticed that the survival of shoots rooted in presence of IBA was much higher compared to that obtained with NAA for the genotype studied.

It should be recognized that there is not one single set of culturing conditions that will be suitable for obtaining complete plantlet for all species or for all genotypes within a species. Tissue culture as a whole is highly dependent on genotypic variations. Adjustment in mineral and plant hormone constituents within the range described in Compositions II and III frequently may be made depending on the species and particular genotype being used. This applies to each of the various stages described above. The adjustments are considered to be within the routine experimental capability of skilled workers in the area of tissue culture. It is understood that many variations can be made in the procedures described for the culturing stages while still retaining the necessary critical compositions of ingredients described in. It is therefore our intention that such variations should be included within the scope of the invention.

We claim:

1. A method for propagating a plant of a bamboo species, said method consisting essentially of:

a) cleaning and sterilizing a nodal bud of the plant;

b) maintaining said nodal bud in a first culture medium for sprouting of buds under conditions and for a time suitable for promoting sprouting of the nodal bud to form a sprouted bud;

c) transferring the sprouted bud to a second culture medium for growth and clonal multiplication of shoots from the sprouted bud; said second medium comprising i) a plurality of salts that collectively comprise elements selected from the group consisting of aluminum, boron, calcium, chlorine, chromium, cobalt, copper, iodine, iron, lead, magnesium, manganese, molybdenum, nitrogen, potassium, phosphorous, silicon, sodium, sulphur, titanium, vandium and zinc, and ii) a plurality of organic components selected from the group consisting of sucrose, glucose, fructose, myoinositol, thiamine hydrochloride, pyridoxine hydrochloride, nicotinic acid, glycine, kinetin, benzyl adenine, malt extract, yeast extract, coconut milk, indolebutyric acid, indoleacetic acid, indolpropionic acid, naphthalene acetic acid and agar;

d) excising the shoots and culturing the excised shoots under conditions and for a time suitable for initiating and promoting development of roots from the shoots whereby to form plantlets therefrom, the culturing of the excised shoots comprising initially placing the excised shoots on a culture medium for root initiation comprising a hormone or hormones which include an auxin and thereafter transferring the excised shoots to a hormone-free medium and maintaining the excised shoots thereon for a time sufficient for the development of the roots; and e) transferring the plantlet or plantlets to soil for growth thereon.

2. A method as claimed in claim 1 wherein said elements (mineral salts) and organic components are present in the following ranges.

|  |  | concentration (mg/L) |
|---|---|---|
| Mineral salts | | |
| K | (salts of potassium) | 96.69 to 1237 |
| $NH_4$ | (salts of ammonium) | 33.75 to 405 |
| Mg | (salts of magnesium) | 5.55 to 47 |
| Ca | (salts of calcium) | 11.92 to 0.136 |
| B | (salts of boron) | 0.13 to 1.4 |
| Al | (salts of aluminum) | 0.1 to 0.0008 |
| Mn | (salts of manganese) | 0.74 to 6.65 |
| $PO_4$ | (phosphate salts) | 52.94 to 174 |
| $NO_3$ | (nitrate salts) | 269.44 to 3754 |
| $SO_4$ | (Sulphate salts) | 59.75 to 914 |
| Cl | (chloride salts) | 21.00 to 241 |
| Fe | (as a chelate with ethylene diamine tetra acetic acid) | 0.50 to 5.25 |
| Co | (salts of cobalt) | 0.0006 to 0.01 |
| Cu | (salts of copper) | 0.0006 to 0.008 |
| Cr | (salts of chromium) | 0.01 to 0.02 |
| Ti | (salts of titanium) | 0.00 to 0.013 |
| V | (salts of vanadium) | 0.00 to 5.45 |
| Zn | (salts of zinc) | 0.23 to 2.73 |
| Mo | (salts of molybdenum) | 0.017 to 0.11 |
| Si | (salts of silicon) | 0.00 to 0.4 |
| Na | (salts of sodium) | 0.081 to 0.65 |
| Pb | (salts of lead) | 0.00 to 0.12 |
| I | (salts of iodine) | 0.017 to 1.15 |
| Cl | (salts of chlorine) | 21 to 241 |
| Organic compounds | | |
| Sucrose | | 20,000 to 50,000 |
| Glucose | | 20,000 to 50,000 |
| Fructose | | 20,000 to 50,000 |
| Myo-Inositol | | 10.75 to 130 |
| Thiamine hydrochloride | | 0.02 to 0.15 |
| Pyridoxine hydrochloride | | 0.075 to 1.75 |
| Nicotinic acid | | 0.05 to 1.5 |
| Glycine | | 0.3 to 3.5 |
| Kinetin | | 0.00 to 0.80 |
| Benzyl adenine | | 0.00 to 0.80 |
| Indolebutyric acid | | 0.0 to 3.5 |
| Indoleacetic acid | | 0.0 to 3.5 |
| Indolepropionic acid | | 0.0 to 3.5 |
| Naphthaleneacetic acid | | 0.0 to 3.5 |
| Malt extract | | 0.00 to 200.00 |
| Yeast extract | | 0.00 to 500.00 |
| Coconut milk (added as mL/L) | | 0.00 to 200.00 |
| Agar (for solidification) | | 4,000 to 4,500 |

3. A method as claimed in claim 1 wherein the mineral salts, and organic components are present in the culture medium for growth and clonal multiplication of in the following ranges:

|  | Concentration mg/L |
|---|---|
| (a) Mineral salts | 1000 to 3198 |
| $KNO_3$ | 1000 to 3198 |
| $NH_4NO_3$ | 772 to 2315 |
| $MgSO_4.7H_2O$ | 223 to 476.5 |
| $CaCl_2.2H_2O$ | 176 to 498.8 |
| $MgSO_4.7H_2O$ | 223 to 476.5 |
| $KH_2PO_4$ | 124.6 to 249.2 |
| $H_3BO_3$ | 2.9739– 8.0068 |
| $AlNH_4(SO_4)_2.12H_2O$ | 0.1176– 0.01344 |
| $MnSO_4.4H_2O$ | 11.7763– 27.004 |
| COOK.COOTi (Salt of titanium) | 0.02382– 0.04423 |
| $NH_4VO_3$ | 0.023– 12.51 |
| $FeSo_4.7H_2O$ (added as chelate with $Na_2EDTA$) | 11.45– 26.13 |
| $CoCl_2.6H_2O$ | 0.1009– 0.04036 |
| $CrO_3$ | 0.01923– 0.03846 |
| $CuSO_4.5H_2O$ | 0.1123– 0.02995 |
| $Na_2O_3Si.9H_2O$ | 0.5059– 4.0475 |
| $ZnSO_4.7H_2O$ | 4.0022– 12.0066 |
| $Na_2MoO_4.2H_2O$ | 0.1764– 0.2773 |
| KI | 0.8066– 4.882 |
| $C_6H_6O_4.Pb.3H_2O$ | 0.1464– 0.2197 |
| $Na_2EDTA.2H_2O$ | 0.6557– 5.2622 |
| Organic components | |
| Sucrose | 20,000.00 50,000.00 |
| Glucose | 20,000.00 50,000.00 |
| Fructose | 20,000.00 50,000.00 |
| myo-Inositol | 75.00 130.00 |
| Thiamine hydrochloride | 0.08 0.15 |
| Nicotinic acid | 0.20 1.50 |
| Pyridoxine hydrochloride | 0.30 1.75 |
| Glycine | 1.20 3.50 |
| Kinetin | 0.20 0.80 |
| Benzyl aminopurine | 0.20 0.80 |
| Malt extract | 50.00 200.00 |
| Yeast extract | 100.00 500.00 |
| Coconut milk (added as ml/L) | 20.00 120.00 |
| Agar agar (for solidification) | 4,000.00 4,500.00 |

4. A method as claimed in claim 1 wherein the mineral salts, and organic components are present in the culture medium for root initiation in following ranges:

|  | Concentration mg/L |
|---|---|
| (a) Mineral salts | |
| $KNO_3$ | 250 to 1600 |
| $NH_4NO_3$ | 150 to 898.8 |
| $MgSO_4.7H_2O$ | 56.27 to 238.26 |
| $CaCl_2.2H_2O$ | 43.72 to 249.4 |
| $KH_2PO_4$ | 75.82 to 303.39 |
| $H_3BO_3$ | 0.7434 to 4.0 |
| $MnSO_4.4H_2O$ | 3 to 13.52 |
| $FeSo_4.7H_2O$ (added as chelate with $Na_2EDTA$) | 2.887 to 13.09 |
| $CoCl_2.6H_2O$ | 0.0024 to 0.02 |
| $CuSO_4.5H_2O$ | 0.0023 to 0.016 |
| $ZnSO_4.7H_2O$ | 1 to 6.02 |
| $Na_2MoO_4.2H_2O$ | 0.043 to 0.151 |
| KI | 0.072 to 2.46 |
| (b) Organic components | |
| Sucrose | 20,000 to 50,000 |
| Glucose | 20,000 to 50,000 |
| Fructose | 20,000 to 50,000 |
| myo-Inositol | 18.75 to 65.00 |
| Thiamine hydrochloride | 0.02 to 0.075 |
| Nicotinic acid | 0.05 to 0.75 |

-continued

| | Concentration mg/L |
|---|---|
| Pyridoxine hydrochloride | 0.075 to 0.875 |
| Glycine | 0.3 to 1.75 |
| Indolebutyric acid | 1.00 to 3.5 |
| Indoleacetic acid | 1.00 to 3.5 |
| Indolepropionic acid | 1.00 to 3.5 |
| Naphthaleneacetic acid | 1.00 to 3.5 |

5. A method as claimed in claim 1 wherein the mineral salts, and the organic components are present in the culture medium for sprouting of buds in the following ranges:

| | Concentration mg/L |
|---|---|
| (a) Mineral salts | |
| $KNO_3$ | 1200 |
| $NH_4NO_3$ | 998.75 |
| $MgSO_4.7H_2O$ | 399.98 |
| $CaCl_2.2H_2O$ | 299.97 |
| $KH_2PO_4$ | 509.71 |
| $H_3BO_3$ | 4.998 |
| $Al.NH_4(SO_4)_2.12H_2O$ | 0.1 |
| $MnSO_4.4H_2O$ | 19.895 |
| $COOK.COOTi$ | 0.027 |
| $NH_4VO_3$ | 0.034 |
| $FeSO_4.7H_2O$ | 15.082 |
| (added as chelate with $Na_2EDTA$) | |
| $Na_2O_3Si.9H_2O$ | 0.6071 |
| $CoCl_2.6H_2O$ | 0.02422 |
| $CrO_3$ | 0.03269 |
| $CuSO_4.5H_2O$ | 0.01964 |
| $ZnSO_4.7H_2O$ | 5.9813 |
| $Na_2MoO_4.2H_2O$ | 0.2622 |
| KI | 1.2034 |
| $C_6H_6O_4.Pb.3H_2O$ | 0.1647 |
| $Na_2EDTA$ | 1.0524 |
| (b) Organic components: | |
| Sucrose | 25,000.00 |
| Glucose | 0.00 |
| myo-Inositol | 100.00 |
| Thiamine hydrochloride | 0.10 |
| Nicotinic acid | 0.40 |
| Pyridoxine hydrochloride | 0.30 |
| Glycine | 1.50 |
| Kinetin | 0.2 |
| Benzyl aminopurine | 0.3 |
| Malt extract | 50.00 |
| Coconut milk (added mL/L) | 50.00 |
| Agar agar (for solidification) | 4,000.00 |

6. A method as claimed in claim 1 wherein the hormone or hormones are selected from the group consisting of indolebutyric acid, indoleacetic acid, indolepropionic acid, napthaleneacetic acid and combinations thereof.

7. A method as claimed in claim 1 wherein the first medium comprises mineral salts, organic nutrients, and a hormone or hormones comprising a cytokinen.

8. A method as claimed in claim 7 wherein the nodal bud is cultured on said first medium at a temperature of about 25°±2° C. for a period of between 20–35 days.

9. A method as claimed in 1 wherein said first medium contains mineral salts, organic nutrients, a cytokinen and an agar in an amount sufficient for solidification of the culture medium, said second medium contains mineral salts, organic nutrients, and a cytokinen, said second medium being in liquid form.

10. A method as claimed in claim 1 wherein the excised shoot or shoots are cultured on said hormone-free medium under alternating light and dark conditions for a period of between 15–35 days.

11. A method as claimed in claim 1 wherein the mineral salts, and organic components are present in the culture medium for shoot growth in the following ranges:

| | Concentration mg/L |
|---|---|
| (a) Mineral salts | |
| $KNO_3$ | 333.35 |
| $NH_4NO_3$ | 199.73 |
| $MgSO_4.7H_2O$ | 74.92 |
| $CaCl_2.2H_2O$ | 58.31 |
| $KH_2PO_4$ | 41.528 |
| $H_3BO_3$ | 1.00 |
| $MnSO_4.4H_2O$ | 3.979 |
| $FeSO_4.7H_2O$ | 3.832 |
| (added as chelate with $Na_2EDTA$) | |
| $CoCl_2.6H_2O$ | 0.0032 |
| $CuSO_4.5H_2O$ | 0.0314 |
| $ZnSO_4.7H_2O$ | 1.319 |
| $Na_2MoO_4.2H_2O$ | 0.0580 |
| KI | 0.0837 |
| (b) Organic components | |
| Sucrose | 10,000 |
| myo-Inositol | 25.00 |
| Thiamine hydrochloride | 0.027 |
| Nicotinic acid | 0.067 |
| Pyridoxine hydrochloride | 0.1 |
| Glycine | 0.4 |
| Indolebutyric acid | 1.0 |

* * * * *